(12) United States Patent
Jain et al.

(10) Patent No.: US 12,318,517 B2
(45) Date of Patent: Jun. 3, 2025

(54) INLINE HEATER FOR A PERITONEAL DIALYSIS SYSTEM

(71) Applicant: MOZARC MEDICAL US LLC, Minneapolis, MN (US)

(72) Inventors: Hemanth Kumar Jain, Bengaluru (IN); Krishnaraja Nellikunje, Bengaluru (IN); Thisanth Gunasekaran, Cumbum (IN)

(73) Assignee: MOZARC MEDICAL US LLC, Minneapolis, MN (US)

( * ) Notice: Subject to any disclaimer, the term of this patent is extended or adjusted under 35 U.S.C. 154(b) by 807 days.

(21) Appl. No.: 17/509,705

(22) Filed: Oct. 25, 2021

(65) Prior Publication Data

US 2023/0128863 A1 Apr. 27, 2023

(51) Int. Cl.
| | | |
|---|---|---|
| *A61M 1/28* | (2006.01) | |
| *A61M 1/14* | (2006.01) | |
| *A61M 1/16* | (2006.01) | |
| *A61M 5/44* | (2006.01) | |

(52) U.S. Cl.
CPC ............ *A61M 1/153* (2022.05); *A61M 1/159* (2022.05); *A61M 1/28* (2013.01); *A61M 1/284* (2014.02); *A61M 1/287* (2013.01); *A61M 2205/127* (2013.01); *A61M 2205/3368* (2013.01); *A61M 2205/36* (2013.01); *A61M 2206/11* (2013.01)

(58) Field of Classification Search
CPC .... A61M 1/153; A61M 1/159; A61M 1/1664; A61M 1/28; A61M 1/284; A61M 1/287; A61M 5/44; A61M 2205/127; A61M 2205/3368; A61M 2205/36; A61M 2206/11
See application file for complete search history.

(56) References Cited

U.S. PATENT DOCUMENTS

| | | |
|---|---|---|
| 5,324,422 A | 6/1994 | Colleran |
| 7,544,300 B2 | 6/2009 | Burbank |
| 7,749,393 B2 | 7/2010 | Brugger |
| 7,976,711 B2 | 7/2011 | Brugger |
| 8,202,420 B2 | 6/2012 | Brugger |
| 8,460,558 B2 | 6/2013 | Brugger |

(Continued)

FOREIGN PATENT DOCUMENTS

| | | |
|---|---|---|
| EP | 0655004 B1 | 6/1999 |
| EP | 1187642 | 3/2002 |

(Continued)

*Primary Examiner* — John Kim (57) ABSTRACT

Systems and devices are provided for heating an infusible liquid. The inline heater includes a fluid flow channel defined by a conduit for flowing an infusible liquid through a first portion of the conduit having a first cross-sectional dimension to a second portion of the conduit having a smaller second cross-sectional dimension. A nozzle is disposed in the first portion of the conduit. A heating element in thermal communication with an outer surface of the second portion of the conduit conducts heat through the conduit into the infusible liquid. The nozzle is positioned to spray the infusible liquid about a circumference of an inner wall of the second portion of the conduit to provide increased heat transfer from the heating element to the infusible liquid. The inline heater may be formed as a cassette for use in a dialysis machine.

6 Claims, 3 Drawing Sheets

(56) References Cited

U.S. PATENT DOCUMENTS

| | | | |
|---|---|---|---|
| 8,585,634 B2 | 11/2013 | Neftel | |
| 9,155,824 B2 | 10/2015 | Eyrard | |
| 9,731,059 B2 | 8/2017 | Crnkovich | |
| 9,861,733 B2 | 1/2018 | Burbank | |
| 9,907,897 B2 | 6/2018 | Burbank | |
| 10,076,599 B2 | 9/2018 | Eyrard | |
| 2003/0220598 A1* | 11/2003 | Busby | A61M 1/155 210/257.2 |
| 2011/0005986 A1* | 1/2011 | Kelly | A61M 60/43 210/321.71 |
| 2011/0297599 A1* | 12/2011 | Lo | A61M 1/1639 210/321.71 |
| 2018/0326138 A1 | 11/2018 | Kalaskar | |
| 2022/0355005 A1* | 11/2022 | Hornsby | A61M 1/1601 |

FOREIGN PATENT DOCUMENTS

| | | |
|---|---|---|
| EP | 1592494 | 6/2009 |
| EP | 2719406 B1 | 5/2016 |
| EP | 3016695 B1 | 5/2016 |
| EP | 2827916 B1 | 8/2017 |
| EP | 3222305 B1 | 9/2017 |
| EP | 2484333 | 11/2017 |
| EP | 1648536 B1 | 12/2017 |
| EP | 3285825 A1 | 2/2018 |
| EP | 3395382 A1 | 10/2018 |
| EP | 3439712 A1 | 2/2019 |

* cited by examiner

INLINE HEATER FOR A PERITONEAL DIALYSIS SYSTEM

FIELD

Systems and devices are provided for heating an infusible liquid. The infusible fluid is any fluid suitable for delivery to a patient. The systems can be used for any application requiring heating a liquid. In one non-limiting embodiment, the systems and devices can be used to heat fluid, such as a peritoneal dialysate, for use in a dialysis therapy, such as peritoneal dialysis.

BACKGROUND

Dialysis is a medical therapy for aiding or replacing kidney function in a patient suffering from renal failure. Dialysis can remove many of the toxins and wastes that a healthy kidney would removes. Dialysis is used to balance the electrolyte or blood salt levels and to remove excess fluid that accumulates in patients with renal failure. Peritoneal dialysis, including automated peritoneal dialysis and continuous ambulatory peritoneal dialysis is a type of dialysis wherein blood is not removed from the body and passed through a dialyzer, but rather a catheter is placed in the peritoneal cavity and a fluid introduced directly into the peritoneal cavity. The fluid infused into the patient's cavity can perform an exchange of solutes across the patient's peritoneal membrane. Because the fluid is introduced directly into the patient, the infused fluid should not only to be free of biological and chemical contaminants, but should also be at a temperature at or near body temperature (37° C.). Dialysate that is too hot or too cold may be uncomfortable and/or hazardous to the patient.

However, the available systems and methods for heating and maintaining the dialysate at or near body temperature require the use of a pan or tray heaters, in which a heater is disposed either external to the tray onto which a bag containing the dialysate is positioned, or inside the tray, and onto which the dialysate bag is positioned during heating. Often these tray heaters include a means to toggle the heater ON/OFF to maintain the dialysate in the bag at body temperature and have a maximum allowable temperature. This type of heating method is often referred to as bulk heating, whereby the dialysate bag is contained within, or disposed external, to the tray for the period of time required to heat the dialysate to a desired temperature. These known systems and methods require an initial setup period, a waiting period for the dialysate to heat and cause a reduction in the flowrate of the dialysate.

As such, there is a need for systems and devices that can provide heating of a fluid without an initial setup, long wait period, and reduction in flow rate. The need includes systems and methods that can provide heating of the dialysate to a desired temperature during peritoneal dialysis therapy for patient safety and comfort. The need includes inline heating of an infusible fluid with appropriate controls for safety, such as sterility. The needs includes avoiding the need. for an external heating such as a tray onto which a bag containing the dialysate is positioned. The need includes a heating an infusible fluid directly from a reservoir, inline, to a infusion line into a patient.

SUMMARY

The technical problem is to provide for systems and methods that can provide on-demand heating to an infusible fluid. The solution is an inline heating system and device that avoids the need for bulk heating. The first aspect of the disclosure relates to an inline heater for infusible liquids. In any embodiment, the heater can include a fluid flow channel defined by a conduit for flowing an infusible liquid from an infusible liquid source through a first portion of the conduit having a first cross-sectional dimension to a second portion of the conduit having a second cross-sectional dimension, wherein the first cross-sectional dimension is less than the second cross-sectional dimension; a nozzle disposed in the first portion of the conduit and having at least one opening to pass the infusible liquid flowing therethrough from the first portion of the conduit to the second portion of the conduit; and a heating element in thermal communication with an outer surface of the second portion of the conduit to conduct heat through the conduit into the infusible liquid; wherein the nozzle sprays the infusible liquid about the circumference of an inner wall of the second portion of the conduit to provide increased heat transfer from the heating element to the infusible liquid.

In any embodiment, the nozzle can include a hollow cone nozzle to spray the infusible liquid in a ring-like spray pattern about the circumference of an inner wall of the second portion of the conduit.

In any embodiment, the nozzle can include a full cone nozzle to spray the infusible liquid in a solid cone-shaped spray pattern about the circumference of an inner wall of the second portion of the conduit.

In any embodiment, the heating element can provide heat to heat the infusible liquid to a predetermined temperature.

In any embodiment, the heating element can transfer heat to the infusible liquid via thermal conduction of the heat from the outer surface of the second portion of the conduit to the inner surface of the second portion of the conduit.

In any embodiment, the heating element is in direct contact with the outer surface of the second portion of the conduit.

The features disclosed as being part of the first aspect of the disclosure can be in the first and third aspect of the disclosure, either alone or in combination.

The second aspect of the disclosure is drawn to a cassette positionable within a cavity of a dialysis machine, the cassette fluidly connectable to a patient and a dialysate source for transferring a dialysate therebetween. In any embodiment, the cassette can include a fluid flow channel defined by a conduit, wherein the dialysate flows from a dialysate source through a first portion of the conduit having a first cross-section to a second portion of the conduit having a second cross-section, wherein the first cross-section is less than the second cross-section; a heating element in thermal communication with an outer surface of the second portion of the conduit to conduct heat through the conduit into the dialysate; and a nozzle disposed in the first portion of the conduit and having at least one opening to spray the dialysate about the circumference of an inner wall of the second portion of the conduit to provide increased heat transfer from the heating element to the dialysate.

In any embodiment, the cassette can include a monitor; the control system programmed to provide the glucose concentration of the patient to at least one of the patient and the monitor.

In any embodiment, the first portion of the conduit is in series with the second portion of the conduit.

In any embodiment, the fluid flow channel can include an inlet and an outlet, the first portion of the conduit being positioned in series between the inlet and the second portion of the conduit, the second portion of the conduit being positioned in series between the first portion of the conduit and the outlet.

In any embodiment, the heating element can transfer heat to the dialysate via thermal conduction of the heat from the outer surface of the second portion of the conduit to the inner surface of the second portion of the conduit.

In any embodiment, the heating element is in direct contact with the outer surface of the second portion of the conduit.

In any embodiment, the cassette is disposable.

The features disclosed as being part of the second aspect of the disclosure can be in the first and third aspect of the disclosure, either alone or in combination.

The third aspect of the disclosure is drawn to a dialysis machine for transferring dialysate to a patient from a dialysate source. In any embodiment, the dialysis machine can include a fluid flow channel in fluid communication with the patient and the dialysate source, the fluid flow channel defined by a conduit, wherein a dialysate flows from the dialysate source through a first portion of the conduit having a first cross-section to a second portion of the conduit having a second cross-section, wherein the first cross-section is less than the second cross-section; a nozzle disposed in the first portion of the conduit, the nozzle having at least one opening to pass the dialysate flowing therethrough; and a heating element in thermal communication with an outer surface of the second portion of the conduit; wherein the nozzle sprays the dialysate about the circumference of an inner wall of the second portion of the conduit to provide increased heat transfer from the heating element to the dialysate.

In any embodiment, the conduit can include an inlet and an outlet, the first portion of the conduit positioned in series between the inlet and the second portion of the conduit, the second portion of the conduit being positioned in series between the first portion of the conduit and the outlet.

In any embodiment, the dialysis machine can include a cavity and a cassette positionable within the cavity, the cassette having contained therein the first portion of the conduit, the second portion of the conduit, and the heating element.

In any embodiment, the heating element provides heat to heat the dialysate to a predetermined temperature.

In any embodiment, the heating element can transfer heat to the dialysate via thermal conduction of the heat from the outer surface of the second portion of the conduit to the inner surface of the second portion of the conduit.

In any embodiment, the heating element is in direct contact with the outer surface of the second portion of the conduit.

In any embodiment, the nozzle can include a hollow cone nozzle.

In any embodiment, the outlet of the conduit is fluidly connectable to a patient line.

In any embodiment, the nozzle provides a turbulent flow of a heated dialysate through the fluid flow channel.

In any embodiment, the dialysis machine further includes a temperature sensor positioned to measure a temperature of the dialysate at an output of the fluid flow channel.

The features disclosed as being part of the third aspect of the disclosure can be in the first and second aspect of the disclosure, either alone or in combination.

DETAILED DESCRIPTION

Unless defined otherwise, all technical and scientific terms used generally have the same meaning as commonly understood by one of ordinary skill in the art.

The articles "a" and "an" are used to refer to one or to over one (i.e., to at least one) of the grammatical object of the article. For example, "an element" means one element or over one element.

The terms "administration," "administering," "administer," "delivering," "deliver," "introducing," and "introduce" can be used, in context, interchangeably to indicate the introduction of a substance to a patient in need thereof, and can further mean the introduction of water, any agent or medication to a peritoneal dialysis circuit where such water, agent or medication will enter the blood of the patient by diffusion, transversal of a diffusion membrane or other means.

The term "cassette" refers to a grouping of components that are arranged together for attachment to, or use with the device, apparatus, or system. One or more components in a cassette can be any combination of single use, disposable, consumable, replaceable, or durable items or materials.

The term "catheter" refers to a flexible tube inserted through a narrow opening into a body cavity.

The term "Chronic kidney disease" (CKD) refers to a condition characterized by the slow loss of kidney function over time. The most common causes of CKD are high blood pressure, diabetes, heart disease, and diseases that cause inflammation in the kidneys. Chronic kidney disease can also be caused by infections or urinary blockages. If CKD progresses, end-stage renal disease (ESRD) can result, where the kidneys' function is inadequate to sustain life without supplemental treatment.

The term "combined peritoneal dialysate effluent line and infusion line" refers to a fluid connector for delivering and removing fluid from a peritoneal cavity of a patient. The combined infusion and effluent line can optionally be separated into an independent infusion line and an independent effluent line.

The terms "communicate", "communicating" and "communication" include but are not limited to, the connection of system electrical elements, either directly or wirelessly, using optical, electromagnetic, electrical or mechanical connections, for data transmission among and between said elements.

The term "communication device" or "communication unit" refers to a device such as a telemetry system or any other alert system such as an audio feedback device, which can communicate monitoring results to a patient and/or a medical care personnel as needed. The term "communication device" in certain instances refers to a device which serves the purpose of sending information with transmission capabilities to another device which receives the information using receiving capabilities. The "communication device" can use electromagnetic, optical or acoustic means for signal transmission.

The terms "component" and "components" refer to a part or element of a larger set or system. As used herein, a component may be an individual element, or may be a grouping of components configured as a set, for example, as a cassette or a cleaning and/or disinfection manifold.

The term "comprising" includes, but is not limited to, whatever follows the word "comprising." Thus, use of the term indicates that the listed elements are required or mandatory but that other elements are optional and may or may not be present.

A "concentrate pump" is a pump configured to move fluid between a concentrate source and a flow path.

A "concentrate solution" is a solution of one or more solutes in water. The concentrate solution can have a solute concentration greater than that to be used in dialysis.

A "concentrate source" is a source of one or more solutes. The concentrate source can have one or more solutes that has a solute concentration greater than the solute concentration to be used for dialysis. The concentrate in the concentrate source can also be lower than the solute concentration generally used in dialysis for generation of low concentration dialysate.

The terms "concentration" and "solute concentration" refers to an amount of a solute dissolved in a given amount of a solvent.

The term "conduit," "circuit" or "flow path" refers to a vessel or passageway having a void volume through which a fluid can travel or move. A conduit can have a dimension parallel to the direction of travel of the fluid that is significantly longer than a dimension orthogonal to the direction of travel of the fluid.

The term "connectable" refers to being able to be joined together for purposes including but not limited to maintaining a position, allowing a flow of fluid, performing a measurement, transmitting power, and transmitting electrical signals. The term "connectable" can refer to being able to be joined together temporarily or permanently.

The term "consisting of" includes and is limited to whatever follows the phrase the phrase "consisting of." Thus, the phrase indicates that the limited elements are required or mandatory and that no other elements may be present.

The term "consumables" refers to components that are dissipated, wasted, spent, or used up during the performance of any function in the present invention. Examples include a quantity of sodium, bicarbonate, electrolytes, infusates, sorbents, cleaning and disinfecting ingredients, anticoagulants, and components for one or more concentrate solutions.

The terms "consumables cartridge" and "consumables container" refer to an object or apparatus having or holding one or more materials that are depleted during operation of the system. The one or more materials may be in solid and/or solution form and can be in separate compartments of the object or apparatus. The object or apparatus may be single use, or may be replenished and used multiple times, for example, by refilling the object to replace the consumed material.

The term "contact" "contacted" or "contacting" refers to (1) a coming together or touching of objects, fluids, or surfaces; (2) the state or condition of touching or of immediate proximity; (3) connection or interaction. For example, in reference to a "dialysate contacting a sorbent material" refers to dialysate that has come together, has touched, or is in immediate proximity to connect or interact with any material or material layer of a sorbent container, system or cartridge.

The term "container" as used herein is a receptacle that may be flexible or inflexible for holding any fluid or solid, such as for example a spent dialysate fluid, or a sodium chloride or sodium bicarbonate solution or solid, or the like.

The term "continuously" refers to an act that occurs repeatedly or constantly, or without interruption or interference, during a given period.

The terms "control," "controlling", or "controls" refers to the ability of one component to direct the actions of a second component.

The term "control signals" refers to energy that is provided from one element of a system to another element of a system to convey information from one element to another or to cause an action. For example, a control signal can energize a valve actuator to cause a valve to open or close. In another example a switch on a valve can convey the open or close state of a valve to a controller.

A "control system" consists of combinations of components that act together to maintain a system to a desired set of performance specifications. The performance specifications can include sensors and monitoring components, processors, memory, and computer components configured to interoperate.

The term "control valve" or "valve" refers to a device that can be operated to regulate the flow of fluid through a conduit or flow path by selectively permitting fluid flow, preventing fluid flow, modifying the rate of fluid flow, or selectively guiding a fluid flow to pass from one conduit or flow path to one or more other conduits or flow paths.

The terms "controlled addition," to "control addition," or "controlling addition" refer to the ability to add one or more substances or fluids to a flow path or container in an accurately controllable amount.

A "controller" or "control unit" is a device which monitors and affects the operational conditions of a given system. The operational conditions are typically referred to as output variables of the system, which can be affected by adjusting certain input variables.

The terms "determining" and "determine" refer to ascertaining a particular state of a system or variable(s).

The term "dextrose solution" refers to mixture of dextrose (glucose) and water, typically delivered intravenously. It is often referred to as a sugar solution and used to treat low blood sugar or provide fluid and electrolyte replenishment.

The term "dialysate" describes a fluid into or out of which solutes from a fluid to be dialyzed diffuse through a membrane. A dialysate typically contains electrolytes that are close in concentration to the physiological concentration of electrolytes found in blood. A common sodium level for dialysate is approximately 140 mEq/L. Normal blood sodium levels can range from approximately 135 mEq/L to 145 mEq/L. The REDY system typically uses dialysate ranging from 120 mEq/L to 160 mEq/L. In certain embodiment, a "predetermined limit" or "predetermined concentration" of sodium values can be based off the common sodium levels for dialysate and normal blood sodium levels. "Normal" saline at 0/9% by weight and commonly used for priming dialyzers and extracorporeal circuits is 154 mEq/L.

A "dialysate container" is any container capable of storing or containing dialysate for dialysis. The container any be of any suitable, size, geometry, or configuration.

The term "dialysate flow path" or "dialysate conduit flow path" refers to any portion of a fluid pathway that conveys a dialysate and is configured to form at least part of a fluid circuit for hemodialysis, hemofiltration, hemodiafiltration or ultrafiltration.

The terms "disposable" and "disposables" refer to any component that is suitable for one or multiple use but requires replacement or refurbishment. Non-limiting examples include a disposable dialyzer, urea sensors, and a degassing module. Disposables can also mean components that have a limited life such as microbial filters, containers, replaceable reservoirs, and the like.

The term "downstream" refers to a position of a first component in a flow path relative to a second component wherein fluid will pass by the second component prior to the first component during normal operation. The first component can be said to be "downstream" of the second component, while the second component is "upstream" of the first component.

A "drain line" is a fluid line for carrying fluid to a drain such as a waste receptacle or drain. The drain line can be connected to a peritoneal cavity of a patient for draining fluid.

The term "effluent line" refers to a fluid connector for removing fluid from a peritoneal cavity of a patient. The term "effluent line" can also refer to a combined effluent and infusion line.

The term "filter" refers to a porous component through which fluid can pass, but that traps one or more materials within the fluid.

A "flow meter" is a device capable of measuring an amount or rate of fluid moving past or through a particular location.

The term "flow path," "fluid flow path" or "fluid flow channel" refers to a route or a collection of routes for a fluid to move within. Within a flow path there may be more than one route that a fluid can follow to move from a first position to a second position. A fluid may move through a flow path such that it recirculates, or passes the same position more than once as it moves through a flow path. A flow path may be a single element such as a tube, or a flow path may be a grouping of components of any type that guide the movement of a fluid. The term "flow loop" and "flow path" often may be used interchangeably.

The term "flow sensor" refers to any component capable of measuring a volume or a rate of fluid moving through a conduit.

The term "flow stream" refers to fluid moving along a flow path.

The term "fluid" can be any substance without a fixed shape that yields easily to external pressure such as a gas or a liquid. Specifically, the fluid can be water containing any solutes at any concentration. The fluid can also be dialysate of any type including fresh, partially used, or spent.

A "fluid characteristic" is any sensed characteristic of a fluid, including temperature, pressure, concentration, color, or any other characteristic.

The term "fluid communication" refers to the ability of fluid to move from one part, element, or component to another; or the state of being connected, such that fluid can move by pressure differences from one portion that is connected to another portion.

The term "fluid manifold" refers to a device capable of carrying a fluid that connects multiple inputs or outputs and provides for the flow of the fluid therethrough.

The term "fluidly connectable," "fluid connection," "fluidly connectable," "fluidically engage", or "fluidically coupled" refers to the ability of providing for the passage of fluid, gas, or combination thereof, from one point to another point. The ability of providing such passage can be any connection, fastening, or forming between two points to permit the flow of fluid, gas, or combinations thereof. The two points can be within or between any one or more of compartments of any type, modules, systems, components, and rechargers.

The term "fluidly connected" refers to a particular state such that the passage of fluid, gas, or combination thereof, is provided from one point to another point. The connection state can also include an unconnected state, such that the two points are disconnected from each other to discontinue flow. It will be further understood that the two "fluidly connectable" points, as defined above, can form a "fluidly connected" state. The two points can be within or between any one or more of compartments, modules, systems, components, and rechargers, all of any type.

The terms "generate peritoneal dialysate" or "peritoneal dialysate generation" refers to creating a peritoneal dialysate solution from constituent parts.

A "heater" is a component capable of raising the temperature of a substance, container, or fluid.

The terms "heating" or to "heat" refer to raising the temperature of a substance, fluid, or container.

The term "hematocrit" refers to the ratio of the volume of red blood cells to the total volume of blood.

The term "in contact" as referred to herein denotes (a) a coming together or touching, as of objects or surfaces; or (b) the state or condition of touching or of being in immediate proximity. "In contact" also includes fluids that are "in fluid communication with" with a solid, such as for example, a fluid, like a dialysate, in contact with a material layer of a sorbent cartridge, or a fluid in contact with a sensor.

The term "infusible," "infusing" "infusion" or to "infuse" a fluid refers to the movement a fluid into an interior space of a living being, such as a mammal. In one non-limiting embodiment, the infusible fluid is a peritoneal dialysate and the interior space is a peritoneal cavity of a patient, such as a human.

An "infusion line" is a fluid line for carrying peritoneal dialysate into a body cavity or part of a patient such as a peritoneal cavity. The term "infusion line" can also refer to a combined effluent and infusion line.

The term "infusion liquid" is a fluid intended for infusion into a patient or subject during a peritoneal dialysis session, such as a peritoneal dialysate.

The term "infusion pump" refers to a device that can perform work on a fluid solution to cause the fluid flow and can actively control the transfer of fluid volume such as an infusate into a circuit.

The term "input/output interface" refers to a module of a processor or computing system that allows data to be received by the processor or computing system and provided by the processor or computing system. The input/output interfaces can automatically receive and provide data from sensors, or can receive data manually input through the interface, such as by a keyboard.

The term "intermittently" refers to an act that occurs with interruption or interference, either repeatedly or constantly, during a given period.

An "integrated cycler" is a component for movement of fluid into and out of the peritoneal cavity of a patient, wherein the integrated cycler forms a part of an overall system. For example, the integrated cycler can be contained in a housing with other components used for peritoneal dialysis and be in fluid and electrical connection with desired components.

The terms "introduce" and "introducing" refer to causing a substance to become present where the substance was not present, or to cause the amount or concentration of a substance to be increased.

An "ion concentrate" refers to one or more ionic compounds. The ion concentrate can have one or more ionic compounds in the ion concentrate. Further, the ion concentrate can have an ion concentration greater than an ion concentration to be used in dialysis.

An "ion concentrate source" refers to a source of one or more ionic compounds. The ion concentrate source can be in water or solid form. The ion concentrate source can further have one or more ionic compounds that are at a higher ion concentration greater than generally used in dialysis.

The term "kidney disease" (KD) refers to a condition characterized by the slow loss of kidney function over time. The most common causes of KD are high blood pressure, diabetes, heart disease, and diseases that cause inflammation in the kidneys. Kidney disease can also be caused by infections or urinary blockages. If KD progresses, the disease can lead to end-stage renal disease (ESRD), where kidney function is inadequate to sustain life without supplemental treatment. KD can be referred to by different stages indicated by Stages 1 to 5. Stage of KD can be evaluated by glomerular filtration rate of the renal system. Stage 1 KD can be indicated by a GFR greater than 90 mL/min/1.73 m.sup.2 with the presence of pathological abnormalities or markers of kidney damage. Stage 2 KD can be indicated by a GFR from 60-89 mL/min/1.73 m.sup.2, Stage 3 KD can be indicated by a GFR from 30-59 mL/min/1.73 m.sup.2 and Stage 4 KD can be indicated by a GFR from 15-29 mL/min/1.73 m.sup.2. A GFR less than 15 mL/min/1.73 m.sup.2 indicates Stage 5 KD or ESRD. KD, as defined herein, contemplates KD regardless of the direction of the pathophysiological mechanisms causing KD and includes CRS Type II and Type IV and Stage 1 through Stage 5 KD among others. Kidney disease can further include acute renal failure, acute kidney injury, and worsening of renal function.

The term "kidney replacement therapy" as used herein describes the use of a provided system to replace, supplement, or augment the function of a patient with impaired kidney function, such as would occur for a patient with Chronic Kidney Disease. An example of a kidney replacement therapy herein includes peritoneal dialysis.

The term "machine-readable storage medium" refers to any electronic device capable of storing information in a digital format for reading by a computer, processor, or other electronic device.

The terms "measuring," to "measure," or "measurement" refer to determining a state or parameter of a system or substance.

The term "memory" refers to any device for recording digital information that can be accessed by a microprocessor, such as RAM, Dynamic RAM, microprocessor cache, FLASH memory, or memory card.

An "osmotic agent" is a substance dissolved in water capable of driving a net movement of water by osmosis across a semi-permeable membrane due to concentration differences of the osmotic agent on each side of the semi-permeable membrane.

An "osmotic agent source" refers to a source of osmotic agents in solid and/or solution form. The osmotic agent source can interface with at least one other module found in systems for dialysis. The osmotic agent source can contain at least one fluid pathway and include components such as conduits, valves, filters, or fluid connection ports, any of which are fluidly connectable to each other or to a fluid flow path. The osmotic agent source can either be formed as a stand-alone enclosure or a compartment integrally formed with an apparatus for dialysis for containing an osmotic agent source.

The term "patient" or "subject" refers to a member of any animal species, preferably a mammalian species, optionally a human. The subject can be an apparently healthy individual, an individual suffering from a disease, or an individual being treated for an acute condition or a chronic disease.

The term "peritoneal cavity" refers to the space between the parietal peritoneum and visceral peritoneum of a patient.

"Peritoneal dialysate" or "peritoneal dialysis fluid" is a dialysis solution to be used in peritoneal dialysis having specified parameters for purity and sterility. Peritoneal dialysate is not the same as dialysate used in peritoneal dialysis although peritoneal dialysate may be used in peritoneal dialysis.

A "peritoneal dialysate generation flow path" is a path used in generating dialysate suitable for peritoneal dialysis.

A "peritoneal dialysate generation system" refers to a collection of components used to generate peritoneal dialysate.

The term "peritoneal dialysis" refers to a therapy wherein a dialysate is infused into the peritoneal cavity, which serves as a natural dialyzer. In general, waste components diffuse from a patient's bloodstream across a peritoneal membrane into the peritoneal dialysis solution via a concentration gradient. In general, excess fluid in the form of plasma water flows from a patient's bloodstream across a peritoneal membrane into the peritoneal dialysis solution via an osmotic gradient.

The term "peritoneal dialysis cycler" or "cycler" refers to components for movement of fluid into and out of the peritoneal cavity of a patient, with or without additional components for generating peritoneal dialysate or performing additional functions.

The term "peritoneal infection" refers to the introduction of an organism into the otherwise sterile peritoneal environment, such as viruses, bacteria, fungi, and parasites.

The term "position" or "positioned" refers to a physical location of a component or system. The term "portion of fluid" refers to an amount of a fluid less than the entire amount of the fluid in a flow path, container, or reservoir.

The term "positioned" refers to the location of a component.

The term "predetermined range" refers to a range of acceptance that was determined by previous events or people rather than by chance.

A "predetermined time" is a set time for an event to occur, such as a set time of day, or a set length of time from a previous event.

The terms "processor," "computer processor," and "microprocessor" as used herein are broad terms and are to be given their ordinary and customary meaning to a person of ordinary skill in the art. The terms refer without limitation to a computer system, state machine, processor, or the like designed to perform arithmetic or logic operations using logic circuitry that responds to and processes the basic instructions that drive a computer. In any embodiment, the terms can include ROM ("read-only memory") and/or RAM ("random-access memory") associated therewith.

The term "programmable," "programmed," and the like as used herein refers to a device using computer hardware architecture and being capable of carrying out a set of commands, automatically.

The term "pump" refers to any device that causes the movement of fluids or gases by the application of suction or pressure.

The terms "pumping," "pumped," or to "pump" refers to moving or flowing a fluid using a pump of any type known to those of ordinary skill in the art.

The terms "pumping fluid" or to "pump fluid" refer to moving a fluid through a flow path with a pump.

A "purified water source" is a water source containing purified water.

"Purified water" can be defined as water produced by distillation, deionization, reverse osmosis, or other suitable processes and meets the definition of "purified water" in the United States Pharmacopeia, 23d Revision, Jan. 1, 1995, and the FDA at 21 CFR Section § 165.110(a)(2)(iv). Other criteria for purified water can be determined by those of skill in the art, particularly as relating to purified water suitable for peritoneal dialysis.

The term "receiving" or to "receive" means to obtain information from any source.

The term "removing" fluid refers to flowing fluid out of a container, system, or patient.

A "reverse osmosis module" is a set of components to drive fluid through one or more semipermeable membranes, wherein pressure is used to move the fluid from a side of the semipermeable membrane with a higher concentration of one or more solutes to a side of the semipermeable membrane with a lower concentration of the one or more solutes.

A "selected time" is a set time chosen by a user or algorithm.

The term "sensor," which can also be referred to as a "detector" in certain instances, and as used herein can be any or combination of a mechanical transducer, converter, optical, electrical, or any other sensing modality that can detect, measure, or sense a physical or otherwise measurable quantity of a matter in a solution, liquid, gas, or combinations thereof. In any non-limiting embodiment, the sensor can measure chemicals, solute concentration, flow, density, content, or any other measurand and convert the obtained value into a signal of any type which can be read by an instrument, circuit, computer, processor, or any other suitable component or device.

The term "sensor element" refers to a device or component of a system that detects or measures a physical property.

The term "sorbent cartridge" refers to a cartridge containing one or more sorbent materials for removing specific solutes from solution. The term "sorbent cartridge" does not require the contents in the cartridge be sorbent based, and the contents of the sorbent cartridge can be any contents capable of removing solutes from a dialysate. The sorbent cartridge may include any suitable amount of one or more sorbent materials. In certain instances, the term "sorbent cartridge" refers to a cartridge which includes one or more sorbent materials besides one or more other materials capable of removing solutes from dialysate. "Sorbent cartridge" can include configurations where at least some materials in the cartridge do not act by mechanisms of adsorption or absorption.

The term "temperature sensor" refers to a device that detects or measures the degree or intensity of heat present in a substance, object, or fluid.

The term "therapy cassette" refers to a detachable set of one or more components that can be connected to an apparatus for performing hemodialysis, hemodiafiltration, or hemofiltration. A connection between a therapy cassette and an apparatus may be for purposes including, but not limited to, maintaining a position, allowing a flow of fluid, performing a measurement, transmitting power, and transmitting electrical signals. A therapy cassette can incorporate at least one fluid pathway, and any one or combination of the following exemplary, non-limiting components such as conduits, fluid connection ports, concentrates, cartridges, valves, sensor elements, reservoirs, filters, vents, dialyzers, heaters, conduits, and disposable and consumable components. A therapy cassette can be configured to interface with at least one other component of a dialysis apparatus such as a dialysate source, to form at least one complete fluid circuit such as a controlled compliant flow path for performing peritoneal dialysis. One or more components in a cassette can be any combination of single use, disposable, consumable, replaceable, or durable items or materials A "sterilization module" is a component or set of components to sterilize a fluid by removing or destroying chemical or biological contaminants.

The term "storing" or to "store" refers to saving electronic data or information in a machine readable medium.

A "temperature sensor" is a sensor capable of determining the temperature of a fluid.

The term "thermal communication" refers to the transfer of heat between two physical systems, whereby there is a flow of thermal energy between the two systems when they are connected by a path permeable to heat.

The term "transmitting" or to "transmit" refers to sending information electronically.

The terms "treating", "treatment" and "therapy" refer to the management and care of a patient having a pathology or condition by administration of one or more therapy contemplated herein. Treating also includes administering one or more methods as described herein or using any of the systems, devices or compositions as described herein in the treatment of a patient. As used herein, "treatment" or "therapy" refers to both therapeutic treatment and prophylactic or preventative measures. "Treating" or "treatment" does not require complete alleviation of signs or symptoms, does not require a cure, and includes protocols having only a marginal or incomplete effect on a patient.

The term "treatment effectiveness" refers to the likelihood that a treatment protocol will benefit patients in a clinical population when administered in clinical practice.

The term "turbulent flow" refers to a fluid motion in which chaotic changes in pressure and flow velocity occur. In contrast, a laminar flow refers to a fluid motion in which fluid flows in parallel layers, with little to no disruption between the layers of the fluid.

An "ultrafilter" is a semi permeable membrane through which a fluid can pass with removal of one or more solutes or particles from the fluid.

The term "upstream" refers to a position of a first component in a flow path relative to a second component wherein fluid will pass by the first component prior to the second component during normal operation. The first component can be said to be "upstream" of the second component, while the second component is "downstream" of the first component.

A "user interface" is a component that allows a user to communicate information or instructions to a processor or a memory device and to receive information or instructions from the processor or memory device.

A "valve" is a device capable of directing the flow of fluid or gas by opening, closing, or obstructing one or more pathways to allow the fluid or gas to travel in a path. One or more valves configured to accomplish a desired flow can be configured into a "valve assembly."

The term "volume" refers to an amount of a fluid.

The term "water purification module" refers to a component or components capable of removing biological or chemical contaminants from water.

A "waste reservoir" is a container for collecting and storing used or waste fluids.

The term "water source" refers to a source from which potable water can be obtained.

Inline Heater for a Peritoneal Dialysis System

Figure 1:
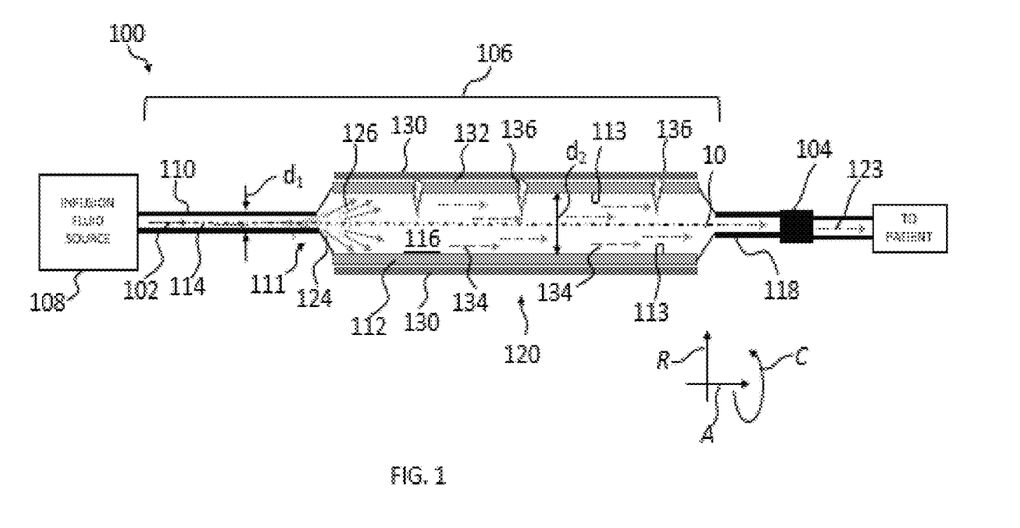
FIG. 1 is a schematic cross-section of an inline heater for heating an infusion fluid during a peritoneal dialysis session in accordance with any embodiment.

Referring now to the drawings, FIG. 1 illustrates an inline heater 100 for use in a peritoneal dialysis system (described presently). In any embodiment, the inline heater 100 can provide for near instant or instant heating of an infusible fluid 102. The infusible fluid can have the appropriate properties for infusion into a body cavity. In one non-limiting example, a peritoneal dialysate to be infused inside a peritoneal cavity should have certain sterility and other suitable chemical, and physical characteristics appropriate for infusion. Any other suitable infusible fluid that requires heating is also contemplated by the invention.

In any embodiment, the infusible fluid is a peritoneal dialysis fluid and more particularly, a peritoneal dialysate fluid, prepared for infusion and/or undergoing infusing. The inline heater 100 provides heating of the infusible fluid 102 from an infusible fluid source, such as a fluid storage bag, while it is flowing from the infusible fluid source to the patient undergoing infusion. The inline heater 100 is fluidly connectable to a patient via a patient fluid line 118. In any embodiment, the inline heater 100 enables intermittent or continuous heating of the infusible fluid, such as a bolus of peritoneal dialysate fluid. In any embodiment, the inline heater 100 may provide for a measure of a temperature of the infusible fluid via a temperature sensor 104 during patient treatment with high accuracy. The inline heater 100 may further provide for calculation and thus monitoring, of the infusible fluid 102 during the peritoneal dialysis treatment.

In any embodiment, the inline heater 100 includes a conduit 106 shown along a fluid flow section of inline heater 100 for flowing the infusible liquid 102 from the infusible fluid source 108. For reference the conduit 106 defines an axial direction A, a radial direction R, and a circumferential direction C, as illustrated. Moreover, the conduit 106 defines an axial centerline or longitudinal axis 10 that extends along the axial direction A for reference purposes, parallel to the direction of flow through the inline heater 100, and to which the conduit 106 is symmetrical. In general, the axial direction A extends parallel to the longitudinal axis 10, the radial direction R extends outward from and inward to the longitudinal axis 10 in a direction orthogonal to the axial direction A, and the circumferential direction C extends three hundred sixty degrees (360°) around the longitudinal axis 10.

The conduit 106 includes a first portion 110 having a first cross-sectional dimension $d_1$ and a second portion 112 having a second cross-sectional dimension $d_2$. The first cross-sectional dimension $d_1$ is less than the second cross-sectional dimension $d_2$. The first portion 110 of the conduit 106 includes an interior bore 114 and the second portion 112 of the conduit includes an interior bore 116. The first portion 110 of the conduit 106 is fluidly coupled to the infusion fluid source 108, such as a bag of dialysate (not shown), at a first end and to the second portion 112 at an opposed second end. The second portion 112 is fluidly coupled at a first end to the first portion 110 and at an opposed second end to a patient fluid line 118. Accordingly, fluid may flow through the first portion 110 and the second portion 112 via a fluid flow channel 120 formed by the fluid communication of bore 114 and bore 116.

The inline heater 100 further includes a nozzle 124 disposed in the first portion 110 of the conduit 106. The nozzle 124 includes at least one opening 126 to pass the infusible liquid 102 flowing therethrough from the first portion 110 of the conduit 106 to the second portion 112 of the conduit 106. The nozzle 120 is positioned at a transition point 111 between the first portion 110 of the conduit 106 and the second point 112 of the conduit 106, or within the first portion 110, in a manner to spray the infusible liquid 102 about a circumference, as indicated by arrow "c", of an inner wall 113 of the second portion 112 of the conduit 106. The nozzle 124 is configured to spray in a pattern, as described below, such that a turbulent flow of the infusible liquid 102 is present in the second portion 112 of the conduit 106. This turbulent flow is in contrast to a laminar flow in which fluid flows in parallel layers, with little to no disruption between the layers of the fluid.

As illustrated, a heater 130 is positioned in thermal communication with the second portion 112 of the conduit 106. In an embodiment, the heater 130, may completely encircle the second portion 112 of the conduit 106 about a circumference of the conduit 106 and extending along an axial length. In an alternate embodiment, the heater 130 may only partially encircle the second portion 112 of the conduit 106 and/or extend along only a portion of the axial length. The heater 130 is positioned proximate an outer surface 132 of the second portion 112 of the conduit 106, such that any air gap formed between the heater 130 and the outer surface 132 of the second portion 112 of the conduit 106 is negligible. In any embodiment, the heater 130 is in contact with the outer surface 132 of the second portion 112 of the conduit 106. The heater 130 is positioned such that the outer surface 132 of the second portion 112 of the conduit 106 is heated according to a preset desired temperature of a resulting heated infusible liquid 134 or according to user input indicative of a desired temperature of the heated infusible liquid 134.

In an embodiment, the inline heater 130 utilizes a PID fuzzy logic temperature controller in which a formula is used to calculate the difference between the desired temperature of the heated infusible liquid 134 and a current temperature of the input infusible liquid 102. The controller predicts how much power to use in to ensure the temperature of the heated infusible liquid 134 remains as close to the setpoint as possible by eliminating the impact of environmental changes.

During heating, heat 136 generated by the heater 130 is transferred to the flowing infusible liquid 102 via conduction from the outer surface 132 of the conduit 106 to the inner surface 113 of the conduit 106, and via convection from the inner surface 113 of the conduit 106 to the flowing infusible liquid 102. As the infusible liquid 102 enters the second portion 112 of the conduit 106 its temperature will start increasing steadily as it flows along the second portion 112 of the conduit 106. As a result, the infusible liquid 102 flowing through the second portion 112 of the conduit is heated, as generally shown by arrows 134, resulting in the heated infusible liquid 134 flowing through the second portion 112 of the conduit. Accordingly, the infusible liquid 102 will enter the second portion 112 of the conduit 106 at an initial temperature and will exit the second portion 112 of the conduit 106 at an increased temperature. Positioning of the heater 130 in contact, or near contact, with the outer surface 132 of the second portion 112 of the conduit 106 provides increased heat transfer from the heater 130 to the infusible liquid 102.

As previously indicated, the second portion 112 of the conduit 106 is fluidically coupled to first portion 110 of the conduit 106 at a first end and to the patient fluid line 118 at a second end. The temperature sensor 104 may be positioned to measure a temperature of the heated infusible liquid 134 at an output of the fluid flow channel 120.

Figure 2A:
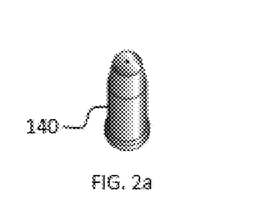
FIG. 2a is a schematic perspective view of a hollow cone nozzle for use in the inline heater of FIG. 1 in accordance with an embodiment.
Figure 2B:
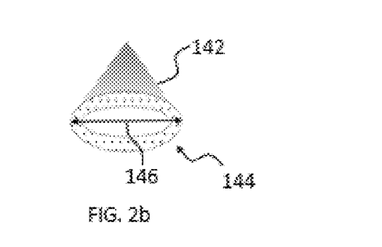
FIG. 2b is a schematic perspective view of a spray pattern of the hollow cone nozzle of FIG. 2a, for use in the inline heater of FIG. 1 in accordance with an embodiment.

Referring now to FIGS. 2a, 2b, 3a and 3b, exemplary designs and spray patterns for nozzle 124 of FIG. 1 are illustrated. More specifically, FIG. 2a illustrates nozzle 124 as a hollow cone nozzle 140, and more particularly, an axial flow hollow cone nozzle. During use, the hollow cone nozzle 140 emits a spray 142 in a ring-like pattern 144 about a given radius 146, as illustrated in FIG. 2b. In any embodiment, the radius 146 of the spray 142 is dimensionally equal to the second cross-sectional dimension $d_2$ of the second portion 112 of the conduit 106, illustrated in FIG. 1. The hollow cone nozzle 140 is capable of producing a small drop size which allows for the spray 142 to have a greater surface area, than a typical full cone nozzle, or the like.

Figure 3A:
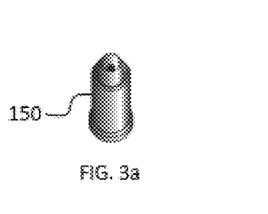
FIG. 3a is a schematic perspective view of a full cone nozzle for use in the inline heater of FIG. 1 in accordance with an embodiment.
Figure 3B:
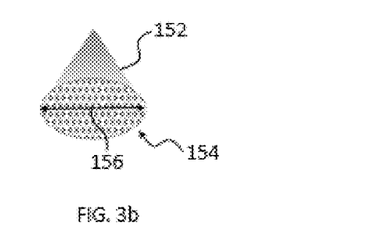
FIG. 3b is a schematic perspective view of a spray pattern of the full cone nozzle of FIG. 2a, for use in the inline heater of FIG. 1 in accordance with an embodiment.

Referring now to FIGS. 3a and 3b, illustrated is a full cone nozzle 150. During use, the full cone nozzle 150 emits a spray 152 in a conical shape, completely within an interior of a circular impact area 156 and in a uniform pattern 154, as illustrated in FIG. 3b. In any embodiment, the circular impact area 156 of the spray 152 is dimensionally equal to the second cross-sectional dimension $d_2$ of the second portion 112 of the conduit 106, illustrated in FIG. 1. Full cone nozzles are capable of producing the conical shape spray 152 by dispersing liquid over the cone's interior.

As previously indicated, by configuring the nozzle 124 to spray in a pattern, and more particularly, to spray in a ring-like pattern 144 or in a conical shaped spray 152, a turbulent flow, in which the infusible liquid 102 undergoes irregular fluctuations and mixing, is present in the second portion 112 of the conduit 106. This turbulent flow of infusible liquid 102, provides increased heat transfer from the heater 130 to the infusible liquid 102.

Figure 4:
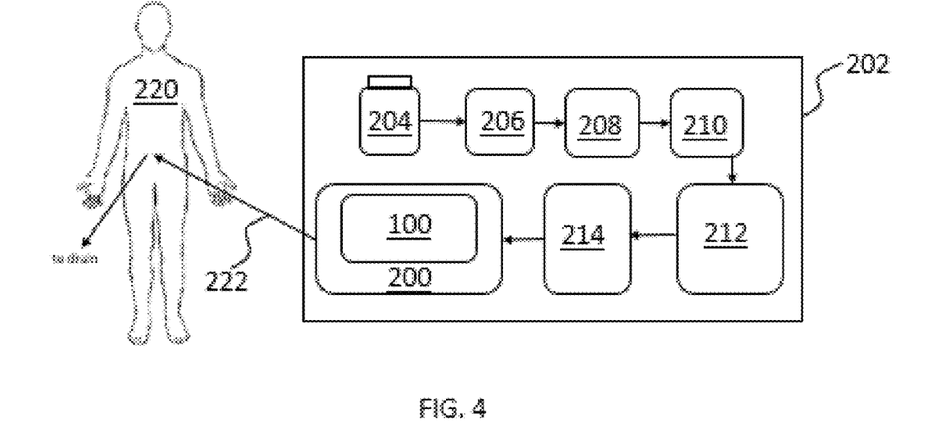
FIG. 4 illustrates a block diagram of a dialysis machine including a cassette having an inline heater for heating an infusion fluid during a peritoneal dialysis session disposed therein in accordance with any embodiment.

In an embodiment, the inline heater 100 of the present invention can provide for inline heating of a dialysate used during peritoneal dialysis therapy and may be configured into a mechanical package that will minimize the burden for storage, transport, setup, operation, and routine maintenance of the therapy system. In some embodiments, the inline heater 100 can be configured within an integrated therapy disposable and consumable cassette 200, as illustrated in FIG. 4, to simplify equipment setup for a therapy session. The therapy cassette 200 can include one or more fluid pathways that is a part of a dialysis machine or system 202 for peritoneal dialysis. The cassette 200 can have one or more fluid pathways wherein connection to the system 202 completes a controlled compliance dialysate flow path that is capable of undergoing inline heating of the dialysate. It will be understood that the therapy cassette 200 can contain a conduit, generally similar to conduit 106 of FIG. 1 as previously described, for providing a flow path and fluid connection ports for connecting the therapy cassette 200 to the system 202 and a patient fluid line 222, generally similar to patient fluid line 118 of FIG. 1. The therapy cassette 200 can also contain any number of concentrates, cartridges, sensor elements, reservoirs, filters, vents to assist in the operation of the system. The therapy cassette 200 may also contain any number of sensors, plumbing and connections necessary to complete a dialysate flow path between the therapy cassette 200 and the dialysis machine 202 and the patient fluid line 222. In particular, the therapy cassette 200 can be configured to interface with at least one other module of the dialysis machine, to form at least one complete fluid circuit such as a controlled compliant flow path for performing peritoneal dialysis.

As illustrated in FIG. 4, the peritoneal dialysis machine 202 is connected to one or more components, of which one or more may be organized into the therapy cassette 200, to complete a controlled compliant flow path. That is, connections can be made within the dialysis machine 202 between the therapy cassette 200, reservoirs such as a water reservoir 204, a sorbent cartridge 206, one or more purification modules 208, a concentrate source 210, one or more filters 212, and a dialysate source 214, to form a controlled compliant flow path for preparation of a physiologically compatible, heated dialysate for delivery to a patient 220. As illustrated herein, the therapy cassette 200 can contain any combination of one or more disposable or consumable therapy components such as the inline heater 100, and sensors such as temperature sensor 104. In any embodiment, the therapy cassette 200 is disposable.

Figure 5:
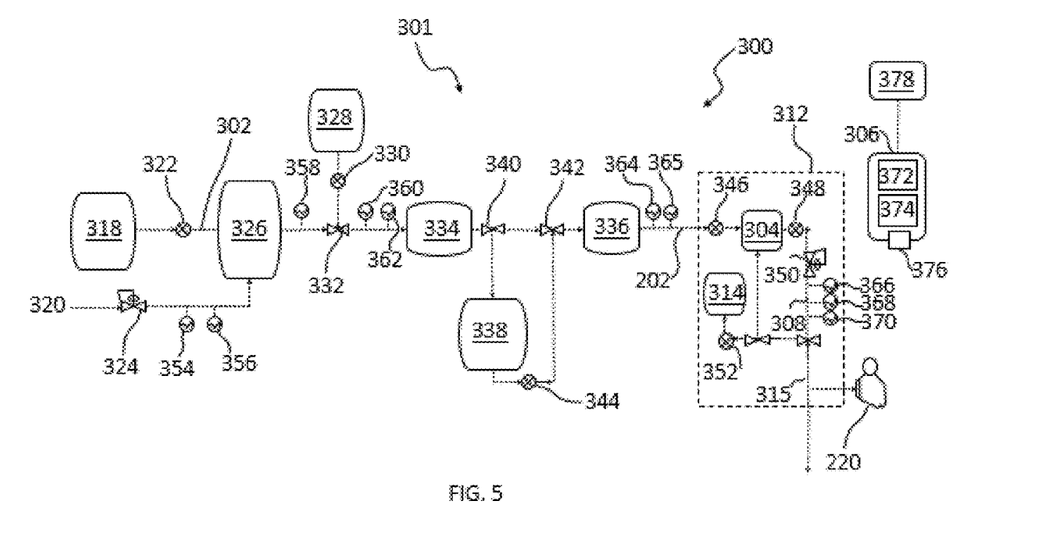
FIG. 5 illustrates a block diagram of a system including an inline heater for heating an infusion fluid during a peritoneal dialysis session in accordance with any embodiment.

FIG. 5 illustrates a detailed system 300 for inline heating of an infusible fluid, such as a peritoneal dialysate, during a peritoneal dialysis session. The system 300 defines a peritoneal dialysate system 301 including a peritoneal dialysate generation flow path 302 and a control system 306, in communication with an inline heater 304, generally similar to the inline heater 100 of FIG. 1, as previously described. The inline heater 304 is positioned to heat the infusible liquid, and more particularly, a peritoneal dialysate intermittently or continuously during a peritoneal dialysis treatment. The control system 306 is programmed to receive a signal from temperature sensor and determine the temperature of the infusible liquid prior to infusion into the patient 220 undergoing peritoneal dialysis. The system 300, as illustrated, includes a combined peritoneal dialysate effluent line and infusion line, referred to herein as a peritoneal dialysate fluid line, or patient line, 308. The peritoneal dialysate fluid line 308 is in fluid communication with a catheter (not shown) having a single channel used for both filling and removal of the peritoneal dialysate fluid from a peritoneal cavity of the patient 310. One of skill in the art will understand that separate effluent and infusion lines can be used. The peritoneal dialysis system 300 is configured to direct the peritoneal dialysate fluid through the inline heater 304 via the peritoneal dialysate fluid line 308 and to the patient 220.

The peritoneal dialysis system 301 can be embodied as a manual peritoneal dialysis system or an automated system including an integrated peritoneal dialysis cycler 312 wherein the peritoneal dialysis cycler 312 includes the peritoneal dialysate fluid line 308 and a portion of the peritoneal dialysate generation flow path 302. Alternatively, the peritoneal dialysis cycler 312 can be nonintegrated with the peritoneal dialysate generation flow path 302, whereby the peritoneal dialysate can be prepared off-line and provided to the cycler 312. In an alternate embodiment, the system may operate manually and not include a cycler. The control system 306 can be a separate device or can be a part of the peritoneal dialysis cycler 312, whether integrated or nonintegrated.

The peritoneal dialysate fluid line 308 can be fluidly connected to a waste reservoir 314 to collect effluent peritoneal dialysate fluid. Optionally, a diverted flow path, such as the drain line 315, can be in fluid communication with the peritoneal dialysate fluid line 308 for analysis of the peritoneal dialysate fluid outside of the peritoneal dialysis cycler 312 and/or directing of the peritoneal dialysate fluid into a drain line 315 if the fluid characteristics in the fluid manifold are outside of a predetermined range. A valve (not shown) in the cycler 312 can divert fluid from the peritoneal dialysate fluid line 308 to the drain line 315 to provide determination of fluid characteristics of the peritoneal dialysate fluid outside of the cycler 312 continuously or at specific intervals and in predetermined amounts.

When used with the integrated cycler 312, the peritoneal dialysate generation flow path 302 can further include a water source, such as a water source 318, one or more water purification modules 326, a concentrate source 328, a sterilization module, such as one or more filters 334 and/or UV light source 336, and the peritoneal dialysis cycler 312. The water source 318, the water purification module 326, the concentrate source 328, the sterilization module 334, 336, and peritoneal dialysis cycler 312 can be fluidly connectable to the peritoneal dialysate generation flow path 302. The peritoneal dialysate generation flow path 302 can be fluidly connected to the peritoneal dialysate fluid line 308 to infuse peritoneal dialysate into the peritoneal cavity of the patient 310.

In an alternate embodiment, either additionally, or as an alternative to a water source 318, the system 300 can use a direct connection to a water source 320. A system pump 322 can control the movement of fluid through the peritoneal dialysate generation flow path 302. If a direct connection to a water source 320 is used, a pressure regulator 324 can ensure that an incoming water pressure is within a predetermined range. The water source 320 can be a non-purified water source, such as tap water, wherein the water from the water source 220 can be purified by the system. A non-purified water source can provide water without additional purification, such as tap water from a municipal water source, water that has undergone some level of purification, but does not meet the definition of "purified water" provided, such as bottled water or filtered water. The water source can contain water meeting the WHO drinkable water standards provided in Guidelines for Drinking Water Quality, World Health Organization, Geneva, Switzerland, 4th edition, 2011. Alternatively, the water source 320 can be a source of purified water, meaning water that meets the applicable standards for use in peritoneal dialysis without additional purification.

The system pumps the fluid from water source 318 or 320 through the water purification module 326 to remove chemical contaminants in the fluid in preparation for creating the peritoneal dialysate. The water purification module 326 can be a sorbent cartridge containing anion and cation exchange resins and/or activated carbon.

After the fluid passes through the water purification module 326, the fluid is pumped to a concentrate source 328, where necessary components for carrying out peritoneal dialysis can be added from the concentrate source 328. The concentrate source 328 can contain one or more solutes for generating the peritoneal dialysate from purified water. In an embodiment, the concentrate source 328 is a dextrose concentrate source containing solid dextrose, wherein adding water to the dextrose solute generates the dextrose concentrate.

The one or more solutes in the concentrate source 328 are utilized to create a peritoneal dialysis fluid that matches a dialysis prescription. A concentrate pump 330 and concentrate valve 332 in communication with the processor or computing unit control the movement of concentrates from the concentrate source 328 to the peritoneal dialysate generation flow path 302 in a controlled addition. Alternatively, the concentrate valve 332 can be a hose T or backflow restricting hose T. The concentrates added from the concentrate source 328 to the peritoneal dialysate generation flow path 302 can include components required for use in peritoneal dialysate. One of skill in the art will understand that any number of concentrate sources can be used, each containing concentrates of one or more substances. For example, the concentrate sources 328 can include any number of concentrates combined or in separate concentrate sources. One or more osmotic agent sources can be included in addition to a single ion concentrate source. Alternatively, multiple ion concentrate sources can be used with each ion concentrate in a separate concentrate source. Any combination of concentrates in any number of concentrate sources can be used. The concentrate sources can infuse each particular concentrate to provide an infused ion concentration that is lower than a prescribed amount for a particular patient. One desired outcome can be to provide a concentration for a particular ion that is lower than a patient's pre-dialysis ion concentration. Additionally, if multiple ion sources are to be delivered by a concentrate source, the present system can selectively dilute a desired ion while maintaining concentration levels for other ions. Hence, the present disclosure can avoid adjusting down every ion insofar as an added diluent may adversely affect concentrations of ions already in a normal range.

Upon addition of solutes from the concentrate source 328, the fluid in the peritoneal dialysate generation flow path 302 can contain all the necessary solutes for peritoneal dialysis. The peritoneal dialysate should reach a level of sterility for peritoneal dialysis such that patients will not contract an infection due to bacteria or other pathogens in fluid used for peritoneal dialysate. The system 300 can pump the fluid to a sterilization module for sterilizing the peritoneal dialysate prior to infusion into the patient 230. As shown in FIG. 5, the sterilization module can include one or more of a filter 334 and a UV light source 336, or any combination thereof. In any embodiment, the sterilization module filter 334 can include a microbial filter, nanofilter, or any filter device inhibiting passage of microfibers or fragments of microbes such as endotoxins in the peritoneal dialysate while allowing the passage of the peritoneal dialysate. In any embodiment, the UV light source 336 can be positioned at any location in the peritoneal dialysate generation flow path 302, including upstream of the filter 334, downstream of the filter 334, or disposed between multiple filters in a multi-filter system. The sterilization module can be any component or set of components capable of sterilizing the peritoneal dialysate.

The generated peritoneal dialysate can be pumped directly to the integrated cycler 312 and through the inline heater 304 for immediate infusion into a patient 220. Alternatively, the dialysate can be pumped to an optional dialysate container 338 as a pre-prepared bolus of solution for storage until ready for use by a patient 310. A plurality of valves 340, 342 can control the movement of fluid to either the dialysate container 338 or the integrated cycler 212. Stored dialysate in dialysate container 338 can be pumped as needed to back into the peritoneal dialysate generation flow path 302 by a pump 344 through valve 342. The dialysate container 338 can store enough peritoneal dialysate for a single infusion of peritoneal dialysate into the patient 220, or enough peritoneal dialysate for multiple or continuous infusions into one or multiple patients.

In an embodiment, the generated peritoneal dialysate can be pumped to a valve (not shown) that can control movement of the peritoneal dialysate to multiple flow options. The peritoneal dialysate can be pumped to the integrated cycler 312 or diverted for use with a non-integrated external cycler (not shown) or to a dialysate container (not shown). All various pumping/diversion options can be performed contemporaneously or selectively. Alternative valve and pump configurations for performing the same functions are contemplated by the present invention. For example, a direct connection to an external cycler can use any type of connector known in the art. The connectors can be single-use or reusable connectors and should provide for sterile transfer of fluids. The connectors should preferably be closed connectors, to avoid contact between the fluids and the external environment.

The integrated cycler 312 can include a valve 348 for metering peritoneal dialysate into the peritoneal cavity of the patient 220. The inline heater 304, generally similar to inline heater 100 of FIG. 1, heats the peritoneal dialysate to a desired temperature prior to infusion into the patient 310. A pressure regulator 350 ensures the peritoneal dialysate pressure is within a predetermined range safe for infusion into the patient 220. A metering pump 346 can use any safe pressure for infusing fluid into the patient 220. Generally, the pump pressures are on average set at ±10.3 kPa or 77.6 mmHg. If there is no fluid flow, the maximum pressure can increase to ±15.2 kPa or 113.8 mmHg for a short period, such as less than 10 seconds. The peritoneal dialysate is infused into the peritoneal cavity of the patient 220 through the fluid line 308. After a dwell period, the peritoneal dialysate is drained from the patient 220 through the fluid line 308, or a separate effluent line (previously described). A pump 352 provides a driving force for removing the peritoneal dialysate from the patient 220. The optional waste reservoir 314 can be included to store the used peritoneal dialysate for disposal. Alternatively, the peritoneal dialysate fluid line 308 can be directly connected to the drain line 315 for direct disposal. The waste reservoir 314 can be any size, including between 12 and 20 L. For patients requiring a higher drainage, a drain manifold can be included for connecting multiple waste reservoirs.

The inline heater 304 may be configured according to any of the embodiments previously described. The inline heater 304 provides heating of the peritoneal dialysate on an intermittent or continual basis during a peritoneal dialysis session. During heating, the inline heater 304 may receive a signal from the control system 306 to heat the peritoneal dialysate to a specific temperature, at or near the body temperature of the patient 220, and a temperature sensor 370 positioned downstream of the inline heater 304, and more specifically between the inline heater 304 and the patient 220, sends a signal of the sensed temperature of the heated peritoneal dialysate to the control system 306, which may or may not provide the obtained data on a monitor or to a user. In any embodiment, in response to temperature data outside of a specified range, the peritoneal dialysis system 300 in response to the signal indicating the temperature being outside the specified range, receives a signal to automatically reroute the peritoneal dialysate back to the inline heater 304 to bring the peritoneal dialysate into the specified range.

Various additional sensors may be utilized by the peritoneal dialysis system 300 to ensure that one or more fluid characteristics of the generated peritoneal dialysate fluid is within predetermined parameters. The additional sensors can be fluidly connected to one or more of the peritoneal dialysate generation flow path 302 and the peritoneal dialysate fluid line 308. The one or more additional sensors can be separate sensors or one or more combined sensors. In an embodiment, one or more additional sensors can be external to the peritoneal dialysis cycler 312. The system an also include duplication of analysis with duplicated sensors in multiple locations. Duplication of the analysis allows calibration of the sensors and acts as a safety check to ensure the sensors are properly functioning. The duplicated sensors can be attached to the cycler 312 or in a standalone system.

The one or more additional sensors may include a flow meter 354 to ensure the incoming water is at a correct flow rate, while a pressure sensor 356 can ensure the incoming water is at an appropriate pressure. A conductivity sensor 358 can be used to ensure that the water exiting the water purification module 326 has been purified to a level safe for use in peritoneal dialysis. A conductivity sensor 360 can ensure the conductivity of the dialysate after the addition of concentrates from concentrate source 328 is within a predetermined range. A pH sensor 362 can ensure the pH of the peritoneal dialysate is within a predetermined range. After passing through the sterilization module including the UV light source 336, a pH sensor 364 and a conductivity sensor 365 can be used to ensure that no changes in the pH or conductivity have occurred during purification or storage of the dialysate in the dialysate container 338. The integrated cycler 312 further may include a flow meter 366, a pressure sensor 368 and the temperature sensor 370, generally similar to temperature sensor 104 of FIG. 1, to ensure that the dialysate being infused into the patient 220 is within a proper flow rate, pressure, and temperature range. One of skill in the art will understand that alternative or additional sensing methods can be used, and any sensor or method known in the art can be incorporated.

The control system 306 can include one or more processors 372, memory 374, and one or more input/output interfaces 376. One of ordinary skill in the art will recognize that the memory 374 can include long-term memory and operating memory, and/or memory serving as both long-term memory and operating memory. The memory 374 can be a machine-readable storage medium. The memory 374 can be in communication with the processor 372 and store instructions that when executed perform any of the methods of the present disclosure. The input/output interface(s) 376 can include an input port to receive information, such as from the inline heater 304 and any of one or more additional sensors, and an output interface to output data to a user, such as an alert notification 378 regarding the sensed data. The processor 372 can be in communication with the inline heater 304 and any of one or more additional sensors and store data received from the inline heater 304 and any of one or more additional sensors in the memory 374. As with all features of the present application, intervening components, such as the input/output interface 376, can be present between the processor 272 and any of one or more additional sensors. The control system 306 can be a stand-alone device independent of the peritoneal dialysis cycler 312 or can be a part of the peritoneal dialysis cycler 312. The control system 306 can be a remote device in network communication with the inline heater 304 and any of one or more additional sensors, such as via the internet. In an embodiment, the dialysis system 300 can include a user interface (not shown) in communication with the control system 306, allowing the patient 220 to direct one or more functions of the system.

In the following exemplary calculation, the fluid considered for calculation is water. The property of the fluid is assumed to be constant with no change in temperature. It is considered that a parallel flow heat exchanger with an outside fluid is always at a constant temperature, i.e., an infinite heat source (maximum temperature of conduit allowed). A resistance component, and more particularly, an air gap between an outside wall of the conduit 106 (FIG. 1) and the heater 130 (FIG. 1) is assumed to be negligible and ignored in the calculation. The below calculation depicts a heater model for heating water from 15° C. to 37° C. flowing at 300 ml/min in a polypropylene tube having an outer diameter of 30.4 mm and a thickness of 0.2 mm. The heater power required to heat the water from 15° C. to 37° C. flowing at 300 ml min is 500 W. The surface area required to transfer the 500 W of heat to the fluid flowing inside the polypropylene tube is 300 ml/min. In an embodiment, a length of the conduit 106 can be reduced from 43.6 cm to 22 cm using the nozzle effect disclosed herein. This occurs due to the entirety of fluid being exposed to the conduit surface area.

The calculation is directly linked to the heat load calculation for the heater. The energy required to heat a fluid with a design factor of 1.1 is calculated in Table 3. The calculations are based on parameters such as mass flowrate fluid and temperature difference in the fluid. Additionally, various thermal parameters, including density, dynamic viscosity, and other parameters of the fluid are used and shown in Table 1. The calculation below assumes that the fluid being heated is water. The length of the tube can also be determined for accommodating the energy and mass flowrate of fluid as shown in Table 2. The calculations also assume a system having a nozzle in place, which directly provides twice the heat transfer capabilities in the system. As shown in Tables 2-3, the length of tube used for the sample calculation is 21.82 cm with a 0.03 cm inner diameter considering the nozzle effect. Using a temperature change from 15-37 C as shown in Table 1, the heating power required is 506.10 W.

TABLE 1

Input for calculation
Input Quantities

| | | |
|---|---|---|
| Inlet Water Temperature | 15 | ° C. |
| Required Water Outlet Temperature | 37 | ° C. |
| Maximum Temp of the fluid Pipe allowed | 80 | ° C. |
| Pipe Inner Dia ($d_i$) | 30 | mm |
| Pipe Inner Dia ($d_o$) | 30.4 | mm |
| Pipe material | Polypropylene | |
| Thermal Conductivity of pipe ($K_{cp}$) | 0.17 | W/m-k |
| Density of Fluid (water) | 999.19 | Kg/m$^3$ |
| Dynamic Viscosity ($\mu$) of Fluid (water) | 0.001139 | Kg/m-s |
| Specific Heat of Fluid (Water) | 4.186 | Kj/Kg-K |
| Thermal Conductivity of Fluid (water) | 0.6 | W/m-K |
| Flow rate of the fluid (water) | 300 | ml/min |

TABLE 2

Output of Thermal model

| | | |
|---|---|---|
| Heater power required considering design factor (1.1) | 506.00 | W |
| Length of pipe required assuming full cross-section is exposed to heater with Design factor (1.1) | 43.60 | cm |
| Length of pipe can reduced using nozzle effect, Because entire set of fluid is getting exposed to surface area | 21.82 | cm |

TABLE 3

Preliminary Calculations

Preliminary Calculation

| | | | |
|---|---|---|---|
| Water Pipe Inner Dia ($d_i$) | 0.0300 | m | |
| Water Pipe Inner Dia ($d_o$) | 0.0304 | m | |
| Ln (r2/r1) | 0.0132 | | |
| Pipe Thickness | 0.0002 | m | |
| Volume Flow Rate of Water | 5.00E−06 | m$^3$/s | |
| Mass Flow Rate of Water | 0.0049960 | Kg/s | |
| Velocity of Flow | 0.007 | m/s | |
| Energy required to heat fluid Q = mCpdT | 460.09 | W | |
| Heater power required considering design factor (1.1) | 506.10 | W | |
| Calculation of Convection Coeficient $h_{(water)}$ | | | |
| Reynolds Number | 186.159 | | (Denisty X Velocity X Diameter)/Dynamic Viscosity |
| Prandtl Number | 7.946 | | (Dynamic Viscosity X Specific Heat)/Conductivity |
| Nusselt Number | 18.079 | | Reference on right hand side |
| Convective Heat Transfer Coefficient ($H_w$) | 361.574 | W/m$^2$-K | H = (k X Nu)/D |
| LMTD for parallel flow heat exchanger ($\Delta TLM$) | 53.245 | ° C. | LMTD - Logarithmic average of the temperature difference reference on right hand side |
| Calculation for Length | | | |
| Resistance Component of fluid flow ($R_{conv1}$) | 0.029 | m-K/W | |
| Thermal Resistance for Pipe (Cylindrical coordinates) ($R_{cyl}$) | 0.012 | m-K/W | |

TABLE 3-continued

| Preliminary Calculations | | |
|---|---|---|
| Resistance Component of air gap between outside wall of the pipe and heater ($R_{conv2}$) | 0.000 | m-K/W |
| Length of Pipe required | 39.679 | cm |
| Length of Pipe required assuming full cross-section is exposed to heater with Design factor (1.1) | 43.65 | cm |

Figure 6:
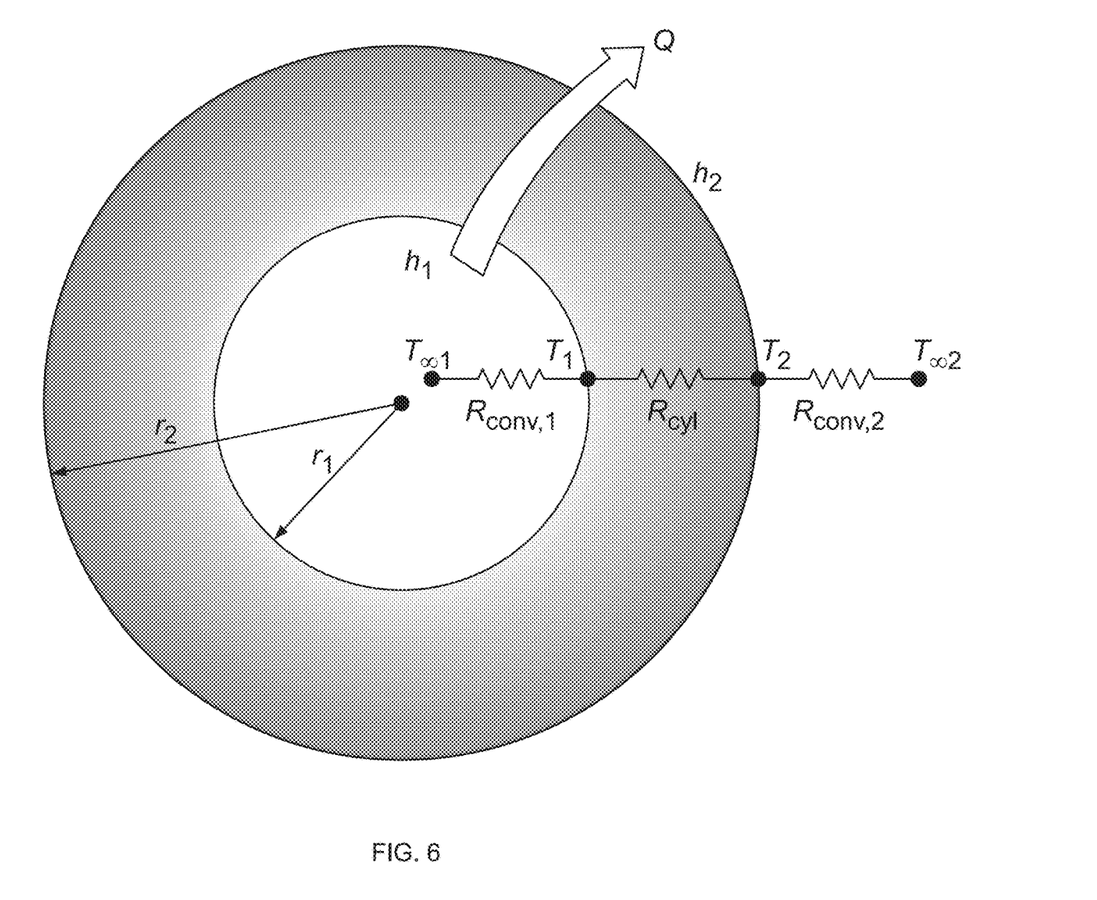
FIG. 6 illustrates a resistive model for a hollow cylinder.

FIG. 6 illustrates a known formula used in the exemplary calculations. More particularly, FIG. 6 illustrates the total resistances for a hollow cylinder in a fluid flow as equal to the resistance component of the fluid flow (Rconv1)+thermal resistance for the pipe (cylindrical coordinates) (Rcy1)+ resistance component of the air gap between the outside wall of the pipe and the heater (Rconv2).

The below formulas are utilized for determining the length of the hollow cylinder, or pipe, in the present disclosure. Length of pipe can reduce the use of the nozzle effect, due to the entire set of fluid being exposed to surface area.

$$R_{total} = R_{conv,1} + R_{cyl} + R_{conv,2}$$
$$= \frac{1}{(2\pi r_1 L)h_1} + \frac{\ln(r_2/r_1)}{2\pi L k} + \frac{1}{(2\pi r_2 L)h_2}$$

and $$Q = UA\Delta T_{LM}$$

$$UA = 1 \bigg/ \left\{ \frac{1}{(2 \times Pi \times r_i \times L \times h_w)} + \frac{\ln\left(\frac{d_o}{d_i}\right)}{(2 \times Pi \times k \times L)} + \frac{1}{(2 \times Pi \times r_o \times L \times h_w)} \right\}$$

$$L = \left\{ Q \times \left[ \frac{1}{(2 \times Pi \times r \times h_w)} + \frac{\ln\left(\frac{d_o}{d_i}\right)}{(2 \times Pi \times k)} + \frac{1}{(2 \times Pi \times r_o \times h_w)} \right] \right\} \bigg/ \Delta T_{LM}$$

Where:

$$h_w = \frac{\text{thermal conductivity of fluid(water)} \times \text{Nusselt Number}}{\text{water pipe inner dia}(d_i)} = \frac{(k \times Nu)}{D}$$

$\Delta T_{LM} = $ LMTD for parallel flow heat exchanger =

$$\frac{(\text{Max temp of fluid pipe allowed} - \text{required water outlet temperature}) - (\text{Max temp of fluid pipe allowed} - \text{inlet water temperature})}{(Ln((\text{Max temp of fluid pipe allowed} - \text{required water outlet temperature}) - (\text{Max temp of fluid pipe allowed} - \text{inlet water temperature})))}$$

$R_{conv,1}$=resistance component of fluid flow $R_{conv,2}$=resistance component of air gap between outside wall of the pipe and heater $R_{cyl}$=thermal resistance for pipe (cylindrical coordinates)

$d_o$=water pipe outer diameter $d_i$=water pipe inner diameter ln=water pipe outer diameter/water pipe inner diameter The following table (Table 4) provides known saturated liquid properties at the different temperatures used in the exemplary calculations.

TABLE 4

Saturated Liquid Properties of Water at Varying Temperatures

| Temperature °C. | Density Kg/m3 | Specific Enthalpy of liquid water Kj/kg | Specific heat Kj/kg · K | Dynamic viscosity Kg/m · s |
|---|---|---|---|---|
| 0 | 999.82 | 0.06 | 4.217 | 0.001792 |
| 1 | 999.89 | 4.28 | 4.213 | 0.001731 |
| 2 | 999.94 | 8.49 | 4.21 | 0.001674 |
| 3 | 999.98 | 12.7 | 4.207 | 0.00162 |
| 4 | 1000 | 16.9 | 4.205 | 0.001569 |
| 5 | 1000 | 21.11 | 4.202 | 0.00152 |
| 6 | 999.99 | 25.31 | 4.2 | 0.001473 |
| 7 | 999.96 | 29.5 | 4.198 | 0.001429 |
| 8 | 999.91 | 33.7 | 4.196 | 0.001386 |
| 9 | 999.85 | 37.9 | 4.194 | 0.001346 |
| 10 | 999.77 | 42.09 | 4.192 | 0.001308 |
| 11 | 999.68 | 46.28 | 4.191 | 0.001271 |
| 12 | 999.58 | 50.47 | 4.189 | 0.001236 |
| 13 | 999.46 | 54.66 | 4.188 | 0.001202 |
| 14 | 999.33 | 58.85 | 4.187 | 0.00117 |
| 15 | 999.19 | 63.04 | 4.186 | 0.001139 |
| 16 | 999.03 | 67.22 | 4.185 | 0.001109 |
| 17 | 999.86 | 71.41 | 4.184 | 0.001081 |
| 18 | 998.68 | 75.59 | 4.183 | 0.001054 |
| 10 | 998.49 | 79.77 | 4.182 | 0.001028 |
| 20 | 998.29 | 83.95 | 4.182 | 0.001003 |
| 21 | 998.08 | 88.14 | 4.181 | 0.000979 |
| 22 | 997.86 | 92.32 | 4.181 | 0.000955 |
| 23 | 997.62 | 96.5 | 4.18 | 0.000933 |
| 24 | 997.38 | 100.68 | 4.18 | 0.000911 |
| 25 | 997.13 | 104.86 | 4.1 | 0.000891 |
| 26 | 996.86 | 109.04 | 4.179 | 0.000871 |
| 27 | 996.59 | 113.22 | 4.179 | 0.000852 |
| 28 | 996.31 | 117.39 | 4.179 | 0.000833 |
| 29 | 996.02 | 121.57 | 4.179 | 0.000815 |
| 30 | 995.71 | 125.75 | 4.178 | 0.000798 |
| 31 | 995.41 | 129.93 | 4.178 | 0.000781 |
| 32 | 995.09 | 134.11 | 4.178 | 0.000765 |
| 33 | 994.76 | 138.29 | 4.178 | 0.000749 |
| 34 | 994.43 | 142.47 | 4.178 | 0.000734 |
| 35 | 994.08 | 146.64 | 4.178 | 0.00072 |
| 36 | 993.73 | 150.82 | 4.178 | 0.000705 |
| 37 | 993.37 | 155 | 4.178 | 0.000692 |
| 38 | 993 | 159.18 | 4.178 | 0.000678 |
| 39 | 992.53 | 163.36 | 4.179 | 0.000666 |
| 40 | 992.25 | 167.54 | 4.179 | 0.000653 |
| 41 | 991.86 | 171.71 | 4.179 | 0.000641 |
| 42 | 991.46 | 175.89 | 4.179 | 0.000629 |
| 43 | 991.05 | 180.07 | 4.179 | 0.000618 |
| 44 | 990.64 | 184.25 | 4.179 | 0.000607 |
| 45 | 990.222 | 188.43 | 4.18 | 0.000596 |
| 46 | 989.8 | 192.61 | 4.18 | 0.000586 |
| 47 | 989.36 | 196.79 | 4.18 | 0.000575 |
| 48 | 988.92 | 200.97 | 4.18 | 0.000566 |
| 49 | 988.47 | 205.15 | 4.181 | 0.000556 |
| 50 | 988.02 | 209.33 | 4.181 | 0.000547 |
| 51 | 987.56 | 213.51 | 4.181 | 0.000538 |
| 52 | 987.09 | 217.69 | 4.182 | 0.000529 |
| 53 | 986.62 | 221.88 | 4.182 | 0.000521 |
| 54 | 986.14 | 226.06 | 4.182 | 0.000512 |
| 55 | 985.55 | 230.24 | 4.183 | 0.000504 |
| 56 | 985.16 | 234.42 | 4.183 | 0.000496 |

TABLE 4-continued

Saturated Liquid Properties of Water at Varying Temperatures

| Temperature °C. | Density Kg/m3 | Specific Enthalpy of liquid water Kj/kg | Specific heat Kj/kg · K | Dynamic viscosity Kg/m · s |
|---|---|---|---|---|
| 57 | 984.56 | 238.61 | 4.183 | 0.000489 |
| 58 | 984.16 | 242.79 | 4.184 | 0.000481 |
| 59 | 983.64 | 246.97 | 4.184 | 0.000474 |
| 60 | 983.13 | 251.16 | 4.185 | 0.000467 |
| 61 | 982.6 | 255.34 | 4.185 | 0.00046 |
| 62 | 982.07 | 259.53 | 4.186 | 0.000453 |
| 63 | 971.54 | 263.72 | 4.186 | 0.000447 |
| 64 | 981 | 267.9 | 4.187 | 0.00044 |
| 65 | 980.45 | 272.09 | 4.187 | 0.000434 |
| 66 | 979.9 | 276.28 | 4.188 | 0.000428 |
| 67 | 979.34 | 280.46 | 4.188 | 0.000422 |
| 68 | 978.78 | 284.65 | 4.189 | 0.000416 |
| 69 | 978.21 | 288.84 | 4.189 | 0.00041 |
| 70 | 977.63 | 290.03 | 4.19 | 0.000404 |
| 71 | 977.05 | 297.22 | 4.19 | 0.000399 |
| 72 | 976.47 | 301.41 | 4.191 | 0.000394 |
| 73 | 975.88 | 305.6 | 4.192 | 0.000388 |
| 74 | 975.28 | 309.79 | 4.192 | 0.000383 |
| 75 | 974.68 | 313.99 | 4.193 | 0.000378 |
| 76 | 974.08 | 318.18 | 4.194 | 0.000373 |
| 77 | 973.46 | 322.37 | 4.194 | 0.000369 |
| 78 | 972.85 | 325.57 | 4.195 | 0.000364 |
| 79 | 972.23 | 330.76 | 4.196 | 0.000359 |
| 80 | 971.6 | 334.96 | 4.196 | 0.000355 |
| 81 | 970.97 | 339.16 | 4.197 | 0.000351 |
| 82 | 970.33 | 343.35 | 4.198 | 0.000346 |
| 83 | 969.69 | 347.55 | 4.199 | 0.000342 |
| 84 | 969.04 | 351.75 | 4.2 | 0.000338 |
| 85 | 968.39 | 355.95 | 4.2 | 0.000334 |
| 86 | 967.73 | 360.15 | 4.201 | 0.00033 |
| 87 | 967.07 | 364.35 | 4.202 | 0.000326 |
| 88 | 966.41 | 368.56 | 4.203 | 0.000322 |
| 89 | 965.74 | 372.76 | 4.204 | 0.000319 |
| 90 | 965.05 | 376.96 | 4.205 | 0.000315 |
| 91 | 964.38 | 381.17 | 4.206 | 0.000311 |
| 92 | 963.7 | 385.38 | 4.207 | 0.000308 |
| 93 | 963.01 | 389.56 | 4.208 | 0.000304 |
| 94 | 962.31 | 393.70 | 4.209 | 0.000301 |
| 95 | 961.62 | 398 | 4.21 | 0.000298 |
| 96 | 960.91 | 402.21 | 4.211 | 0.000295 |
| 97 | 960.2 | 406.42 | 4.212 | 0.000291 |
| 98 | 959.49 | 410.64 | 4.213 | 0.000288 |
| 99 | 958.78 | 414.85 | 4.214 | 0.000285 |
| 100 | 958.05 | 419.06 | 4.216 | 0.000282 | http://www.thermexcel.com/english/tables/eau_atm.htm

The disclosed system for heating a peritoneal dialysate during a peritoneal dialysis session via an inline heater to temperature in a specified range and the rerouting of the dialysate back to the inline heater during the session to address a temperature of the dialysate being outside of a specified range ensures patient comfort and safety during the peritoneal dialysis session.

The particular embodiments disclosed above are illustrative only and may be modified and practiced in different but equivalent manners apparent to those skilled in the art having the benefit of the teaching provided herein. Furthermore, no limitations are intended with respect to the details of construction, or the design shown herein, other than as described in the claims below. One skilled in the art will understand that various combinations and/or modifications and variations can be made in the systems and methods depending upon the specific needs for operation. Features illustrated or described as being part of an aspect as described herein can be used in any other aspect as described herein, either alone or in combination.

What is claimed is:

1. A cassette positionable within a cavity of a dialysis machine, the cassette fluidly connectable to a patient and a dialysate source for transferring a dialysate therebetween, the cassette comprising:
   a fluid flow channel defined by a conduit, wherein the dialysate flows from a dialysate source through a first portion of the conduit having a first cross-section to a second portion of the conduit having a second cross-section, wherein the first cross-section is less than the second cross-section;
   a heating element in thermal communication with an outer surface of the second portion of the conduit to conduct heat through the conduit into the dialysate; and
   a nozzle disposed in the first portion of the conduit and having at least one opening to spray the dialysate about the circumference of an inner wall of the second portion of the conduit to provide increased heat transfer from the heating element to the dialysate.

2. The cassette of claim 1, wherein the first portion of the conduit is in series with the second portion of the conduit.

3. The cassette of claim 1, wherein the fluid flow channel includes an inlet and an outlet, the first portion of the conduit being positioned in series between the inlet and the second portion of the conduit, the second portion of the conduit being positioned in series between the first portion of the conduit and the outlet.

4. The cassette of claim 1, wherein the heating element transfers heat to the dialysate via thermal conduction of the heat from the outer surface of the second portion of the conduit to the inner surface of the second portion of the conduit.

5. The cassette of claim 1, wherein the heating element is in direct contact with the outer surface of the second portion of the conduit.

6. The cassette of claim 1, wherein the cassette is disposable.

* * * * *